United States Patent [19]
Gianturco

[11] Patent Number: 5,334,210
[45] Date of Patent: Aug. 2, 1994

[54] VASCULAR OCCLUSION ASSEMBLY

[75] Inventor: Cesare Gianturco, Savoy, Ill.

[73] Assignee: Cook Incorporated, Bloomington, Ind.

[21] Appl. No.: 45,414

[22] Filed: Apr. 9, 1993

[51] Int. Cl.$^5$ .............................................. A61B 17/12
[52] U.S. Cl. .................................... 606/151; 606/195
[58] Field of Search ............... 606/108, 195, 213, 151, 606/198

[56] References Cited

U.S. PATENT DOCUMENTS

| | | | |
|---|---|---|---|
| 4,638,803 | 1/1987 | Rand | 606/195 X |
| 4,773,393 | 9/1988 | Haber et al. | 606/195 |
| 5,108,407 | 4/1992 | Geremia et al. | 606/108 |
| 5,108,420 | 4/1992 | Marks | |

OTHER PUBLICATIONS

William A. Cook Australia Pty. Ltd., *Detachable Vascular Occlusive Balloon and Catheter Delivery System Including Cook "Peel-Away" Loading System*, May 1991, Eight Mile Plains, Australia.

*Primary Examiner*—Michael H. Thaler
*Attorney, Agent, or Firm*—Richard J. Godlewski

[57] ABSTRACT

A vascular occlusion assembly for therapeutically occluding a vascular site in a patient. The assembly comprises a foldable material occlusion bag having an expanded diamond shape and an elongated flexible filler member which is inserted in the internal cavity of the occlusion bag. When positioned in the internal cavity of the bag, the filler member assumes a convoluted configuration expanding the bag to the expanded shape. The occlusion bag is positioned on the flared distal end of a positioning catheter. A collar is wrapped around the neck of the bag to securely position the bag and prevent premature detachment from the positioning catheter. A pusher catheter is coaxially positioned around the positioning catheter to release the expanded occlusion bag from the flared distal end of the positioning catheter. A handle is releasably attached to the proximal end of the flexible filler member and inserted into the positioning catheter for expanding the occlusion bag to the diamond shape. The distal portion of the filler member is hook-shaped for readily inserting the filler member in the bag without tearing the bag. The distal end segment of the filler member is also enlarged to minimize perforation of the bag and prevent withdrawal through the positioning catheter.

20 Claims, 2 Drawing Sheets

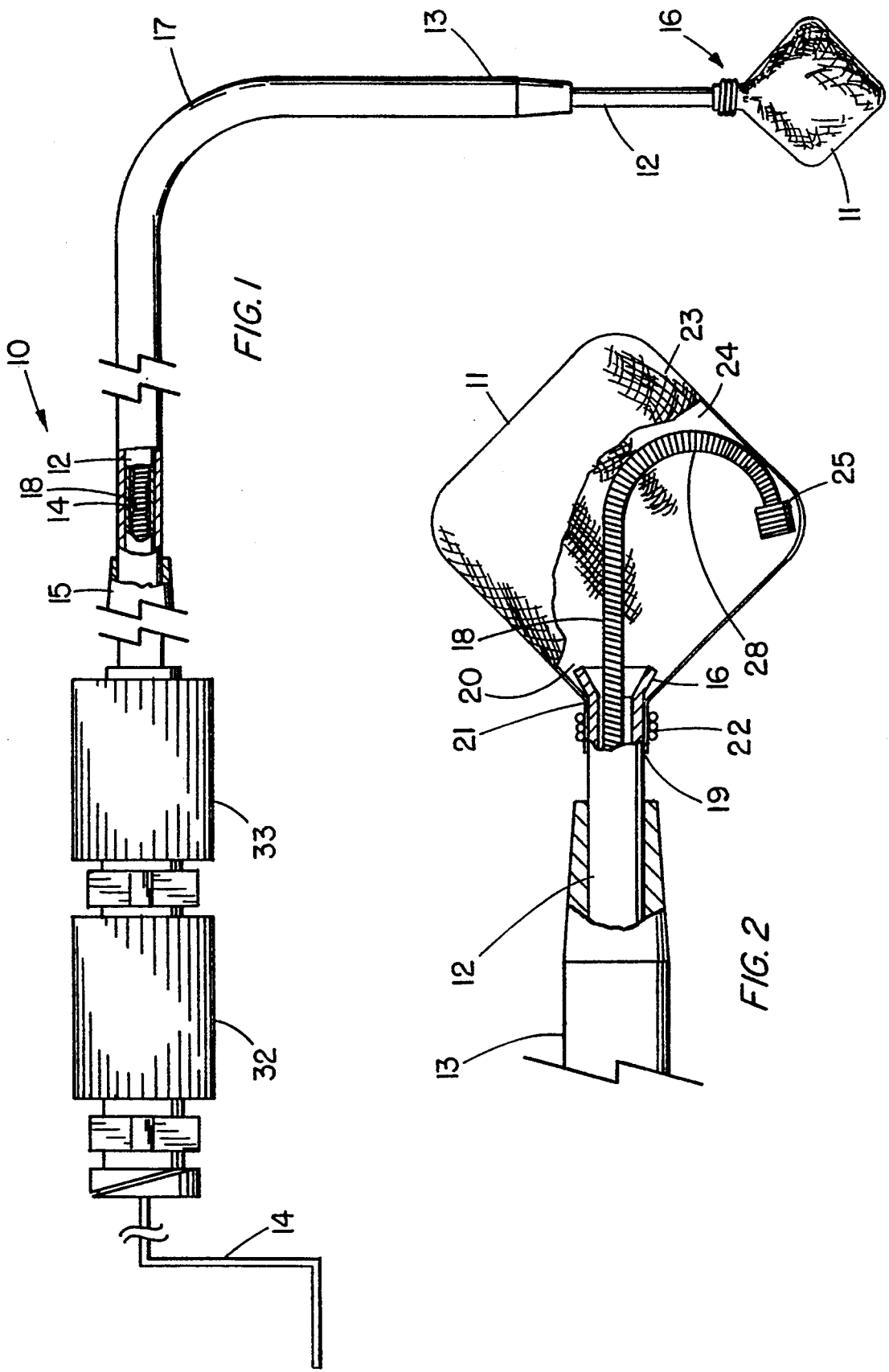

VASCULAR OCCLUSION ASSEMBLY

TECHNICAL FIELD

This invention relates generally to vascular occlusion devices and particularly to a vascular occlusion device utilizing a foldable material occlusion bag that is expanded with a convoluted flexible member positioned within the bag.

BACKGROUND OF THE INVENTION

Catheters for performing a therapeutic embolization procedure typically have detachable, inflatable balloons formed of latex or a C-FLEX TM material. During an embolization procedure, the detachable balloon is attached to the distal end of a delivery catheter and positioned at the treatment site using a visualization aid such as fluoroscopy. Once positioned, the balloon is filled with a solidifying gelatinous fluid until a predetermined pressure is reached within the balloon for forcing the balloon valve closed and away from the delivery catheter. In this manner, the balloon is detached from the delivery catheter. The gelatinous fluid quickly solidifies for achieving long-term occlusion of the blood vessel at the treatment site.

A problem with these detachable balloons is that there is no positive means of detachment. Detachment of a balloon depends on fluid forces in the balloon and in the bloodstream at the treatment site. Blood flow surrounding the balloon on the delivery catheter potentially causes premature balloon detachment. As a result, the balloon is not filled with gelatinous fluid, and the balloon valve is not sealed. The partially collapsed balloon moves through the vascular system of a patient to an undesirable site such as the heart, brain, or lungs to cause a heart attack, stroke, or pulmonary embolism and possibly death.

SUMMARY OF THE INVENTION

The foregoing problems are solved and a technical advance is achieved in an illustrative vascular occlusion assembly including a foldable material occlusion bag having an expanded, volumetric diamond shape and an elongated filler member which is inserted in the cavity of the occlusion bag and assumes a convoluted configuration expanding the bag to the expanded shape.

The assembly further includes a positioning catheter having a flared distal end which is positioned in the internal cavity of the occlusion bag for positioning the bag at an occlusion site in the vascular system of a patient. The occlusion bag includes a neck between an external opening and the internal cavity thereof. The neck is positioned proximally from the flared distal end of the positioning catheter. A collar is wrapped around the neck and positioning catheter to advantageously secure the bag to the positioning catheter during delivery to the occlusion site.

The assembly also includes a pusher catheter coaxially positioned around the positioning catheter for pushing the expanded occlusion bag off the flared distal end of the positioning catheter when positioned at the occlusion site. The distal portions of the pusher and positioning catheters include a curved distal portion for directional control during positioning of the assembly in the vascular system of the patient.

The flexible member comprises a helical coil having a hook-shaped distal portion for ready insertion into the internal cavity of the bag. The foldable material bag is preferably formed from pieces of rip stop nylon material heat sealed about the circumference thereof. The rip stop nylon advantageously minimizes tearing should the hook-shaped distal portion of the flexible member engage the material. The distal end segment of the flexible member has a cross-sectional dimension larger than the remainder of the member to further advantageously prevent or minimize tearing of the rip stop nylon and to prevent withdrawal of the flexible filler member back through the positioning catheter.

The assembly yet further includes a handle which is positioned in the passage of the hollow passage of the positioning catheter and releasably attached to the proximal end of the flexible elongated member.

The surgical procedure for introducing the foldable material bag to the occlusion site includes positioning the elongated flexible member and the handle releasably attached thereto in the positioning catheter. The foldable material bag along with the positioning and pusher catheters are introduced to the vascular occlusion site using, for example, Seldinger technique. The flexible filler member is pushed into the internal cavity of the foldable material bag with the handle, thereby causing the filler member to assume a convoluted configuration and expanded the bag to a volumetric diamond shape. The handle is then released from the flexible filler member and the foldable material bag is pushed with the pusher catheter from the flared distal end of the positioning catheter.

BRIEF DESCRIPTION OF THE DRAWING

FIG. 1 depicts a partially sectioned, longitudinal view of an illustrative vascular occlusion assembly of the present invention;

FIG. 2 depicts an enlarged view of the distal end of the assembly of FIG. 1;

DETAILED DESCRIPTION

Figure 3:
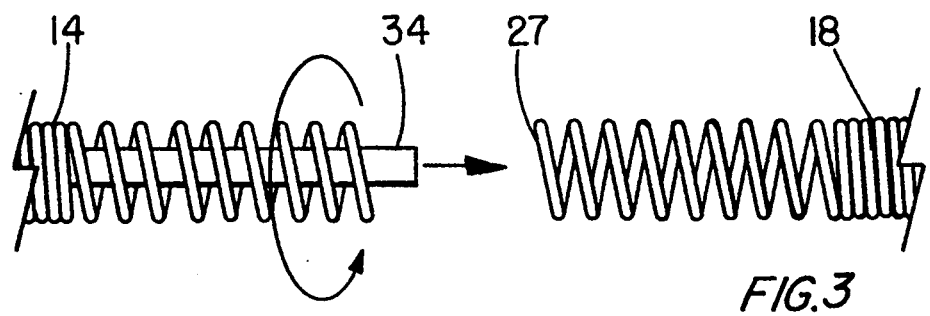
FIG. 3 depicts a longitudinal view of the releasable attachment of the handle and elongated flexible member of the assembly of FIG. 1 in a detached condition.

FIG. 1 depicts a partially sectioned, longitudinal view of an illustrative vascular occlusion assembly 10 including foldable material occlusion bag 11, positioning catheter 12, pusher catheter 13, handle 14, and introducer sheath 15. The foldable material occlusion bag is positioned about flared distal end 16 of the positioning catheter, which is more clearly depicted in FIG. 2. The introducer sheath and the positioning and pusher catheters are coaxially positioned for introduction and release of the occlusion bag at a desirable site in the vascular system of a patient. Pusher catheter 13 includes curved distal portion 17 for directional control of the vascular occlusion assembly in the vascular system. Coaxial positioning catheter 12 similarly includes a curved distal portion (not shown). Coaxial catheters 12 and 13 are fixedly positioned relative to each other with well-known interconnecting proximal hubs 32 and 33, respectively.

Vascular occlusion assembly 10 further includes elongated flexible member 18, which is releasably attached to handle 14. In use, the elongated flexible member 18 is positioned in the foldable material bag for filling the bag to an expanded diamond shape which occludes the vessel.

FIG. 2 depicts an enlarged view of foldable material occlusion bag 11 including external opening 19, which communicates with internal cavity 20, and neck 21, which is positioned between the external opening and internal cavity. Foldable material occlusion bag 11 further includes collar 22 positioned around neck 21 for retaining flared distal end 16 of positioning catheter 12 in the internal cavity of the foldable material bag. Collar 22 comprises, for example, several turns of 0.004" diameter platinum wire wrap such as commercially available tungsten/platinum alloy #479 wire. Collar 22 is attached to neck 21 by commercially available medical grade adhesive. The foldable material bag comprises, for example, mated pieces 23 and 24 of untreated rip stop nylon attached together about the circumference thereof by heat sealing or any other well-known attachment method. The foldable material occlusion bag is generally diamond shaped and preferably measures in a range from 3 to 9 mm wide.

Elongated flexible member 18, or filler member 18, includes enlarged distal end segment 25 for preventing protrusion and release of the elongated flexible member through the foldable material occlusion bag when member 18 is positioned therein. The enlarged cross-sectional dimension of distal end segment 25 prevents puncture of the foldable material bag. Additionally, the enlarged distal end segment prevents the filler member from being pulled back through the positioning catheter. Elongated flexible member 18 comprises, for example, a helical coil with proximal end 27 as depicted in FIG. 3 and preformed hook-shaped distal portion 28. Elongated flexible member 18 comprises, for example, an appropriate length of 0.025" diameter stainless steel coil to fill the occlusion bag. Enlarged distal end segment 25 comprises, for example, a 0.050" length of 0.045" diameter stainless steel coil welded to the distal end of member 18.

Pusher catheter 13 comprises, for example, an 86 cm length of 7.5 French, 0.0985" outside diameter, TEFLON ™ radiopaque tubing material. Positioning catheter 12 comprises, for example, an 87 cm length of 4 French 0.053" outside diameter, TEFLON ™ radiopaque tubing material.

FIG. 3 depicts a longitudinal view of the releasable attachment of handle 14 and proximal end 27 of elongated flexible member 18 in a detached condition. The handle and member are attached by rotating the handle for engaging or attaching the mating coils. Prior to introduction into the vascular system of a patient, the vascular occlusion assembly is coaxially positioned with handle 14 and elongated flexible member 18 releasably attached at proximal end 27 thereof and positioned in the positioning catheter.

Elongated flexible member 18 has, for example, a 6 to 8 mm length of coils about proximal end 27 that are spaced from each other approximately 0.010 mm. The preformed hook-shaped distal portion has, for example, an approximately 2.5 mm J-curve. Handle 14 comprises, for example, a 73.5 cm length of 0.025" diameter stainless steel coil with a 6 to 8 mm length of distal coils that are separated from each other approximately 0.010 mm and positioned around distal end mandril wire 34. The separated handle coils mate with the separated, proximal end member coils around the mandril wire for releasably attaching the handle and member. A length of platinum wire is wrapped for a length of 2 to 3 mm between the most proximal of the separated coils of the handle. The platinum wire wrap is attached to the stainless steel coils by soldering or any other well-known method. The proximal end of the stainless steel coil forming the handle is soldered to an appropriate length of 23 gauge cannula. The length of cannula includes two right angle bends with a proximally extending straight portion approximately 2 cm long.

The appropriate lengths of the stainless steel coils of the handle and elongated flexible member are varied depending on the size of the foldable material occlusion bag. For example, a 3 mm wide bag is preferably used with a 10.5 cm length of flexible member coil and an 83.5 cm length of handle coil; a 5 mm wide occlusion bag is preferably used with an 18 cm length of flexible member coil and a 91 cm length of handle coil; a 7 mm wide bag is preferably used with a 31 cm length of flexible member coil and a 104 cm length of handle coil; and a 9 mm wide bag is preferably used with a 53 cm length of flexible member coil and a 126 cm length of handle coil.

Figure 4:
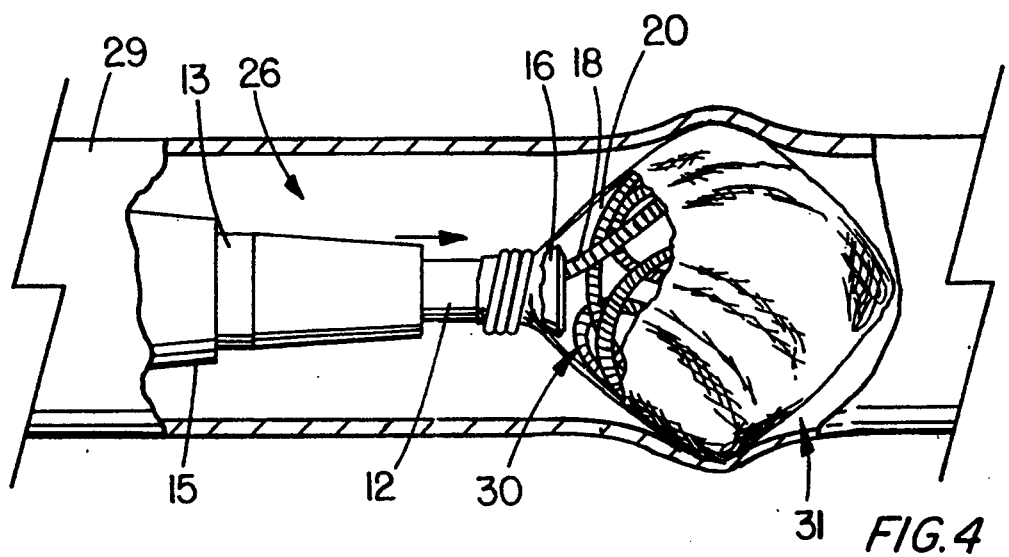
FIG. 4 depicts a partially sectioned, longitudinal view of the assembly of FIG. 1 positioned in a blood vessel with the foldable material occlusion bag in an expanded shape.

FIG. 4 depicts a partially sectioned, longitudinal view of the foldable material occlusion bag of the coaxial vascular occlusion assembly that is percutaneously positioned in a vascular site such as blood vessel 29 using the well-known Seldinger technique. Flexible elongated member 18, or filler member 18, is positioned in internal cavity 20 of the foldable material occlusion bag by pushing distally on the handle. The preformed hook-shaped portion of the filler member facilitates bending of the member into convoluted configuration 30 during advancement into the cavity of the foldable material occlusion bag. When the flexible elongated member is convoluted and positioned in the folded material occlusion bag, the bag assumes expanded shape 31, which is generally a volumetric diamond configuration. The handle is rotated proximally for detaching or releasing the handle from the flexible elongated member. Beveled distal end 26 of pusher catheter 13 is advanced from introducer sheath 15 and along positioning catheter 12 to engage and release neck 21 of the expanded occlusion bag from flared distal end 16 of the positioning catheter.

Figure 5:
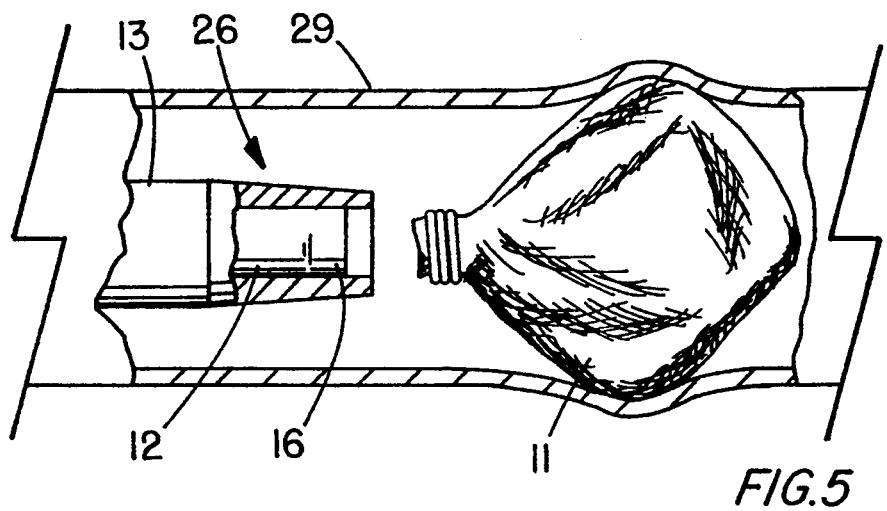
FIG. 5 depicts a partially sectioned, longitudinal view of the assembly of FIG. 4 with the foldable material occlusion bag expanded and released from the positioning catheter.

FIG. 5 depicts a partially sectioned, longitudinal view of beveled distal end 26 of pusher catheter 13. Beveled distal end 26 of the pusher catheter provides for releasing the foldable material occlusion bag from flared distal end 16 of the positioning catheter. The pusher catheter is advanced distally over flared distal end 16 of the positioning catheter for flattening or compressing the flare. When the flare is compressed, the expanded occlusion bag is readily released from the positioning catheter.

It is to be understood that the above-described vascular occlusion assembly is merely an illustrative embodiment of the principles of this invention and that other variations of the assembly, such as the release attachment of the handle and filler member, the preformed shape of the distal portion of the filler member, or the shape of the occlusion bag, may be devised by those skilled in the art without departing from the spirit and scope of this invention.

What is claimed is:

1. A vascular occlusion assembly comprising:

a foldable material bag having an expanded shape, an internal cavity, and an external opening communicating with said internal cavity; and an elongated flexible member which is inserted in said internal cavity through said external opening of said foldable material bag and when positioned in said internal cavity of said foldable material bag assumes a convoluted configuration expanding said foldable material bag to said expanded shape without being fixedly secured thereto, said vascular occlusion assembly adapted to be placed within the vascular system to occlude the same.

2. The assembly of claim 1 wherein said foldable material bag further comprises a neck positioned between said external opening and said internal cavity.

3. The assembly of claim 2 further comprising a wire wrap positioned around said neck.

4. The assembly of claim 1 wherein said foldable material bag comprises first and second pieces of rip stop nylon attached together proximate a circumference thereof.

5. The assembly of claim 1 wherein said expanded shape is a volumetric diamond configuration.

6. The assembly of claim 1 further comprising a positioning catheter having a flared distal end positioned in said internal cavity of said foldable material bag.

7. The assembly of claim 6 wherein said positioning catheter has a curved distal portion.

8. The assembly of claim 6 wherein said foldable material bag further comprises a neck positioned between said external opening and said internal cavity and wherein said assembly further comprises a collar positioned around said neck.

9. The assembly of claim 6 further comprising a pusher catheter coaxially positioned around said positioning catheter.

10. The assembly of claim 9 wherein said pusher catheter has a curved distal portion.

11. The assembly of claim 6 further comprising a handle positioned in said positioning catheter and releasably attached to a proximal end of said elongated flexible member.

12. The assembly of claim 11 further comprising a method of using the assembly comprising the steps of:
positioning said elongated flexible member and said handle releasably attached thereto in said positioning catheter;
introducing said foldable material bag to a vascular site in a patient;
pushing said elongated flexible member with said handle into said internal cavity of said foldable material bag;
releasing said handle from said elongated flexible member when said member is positioned in said internal cavity of said foldable material bag; and
pushing said foldable material bag from said flared distal end of said positioning catheter with said pusher catheter.

13. The assembly of claim 1 wherein said elongated flexible member comprises a helical coil having a hook-shaped distal portion.

14. The assembly of claim 1 wherein said elongated flexible member includes a distal end segment having a cross-sectional dimension larger than a remainder of said elongated flexible member.

15. A vascular occlusion assembly comprising:
a foldable material bag having an expanded shape, an internal cavity, a neck, and an external opening communicating with said internal cavity through said neck;
a positioning catheter having a flared distal end positioned in said internal cavity of said foldable material bag; and
a filler member formed from a solid material positioned in said positioning catheter and when positioned in said internal cavity of said foldable material bag assuming a convoluted configuration expanding said foldable material bag to said expanded shape without being fixedly secured thereto, said bag with said filler material positioned therein adapted to be placed within the vascular system to occlude the same.

16. The assembly of claim 15 further comprising a collar positioned around said neck and a pusher catheter coaxially positioned around said positioning catheter and having a distal end for releasing said foldable material bag from said flared distal end of said positioning catheter when said filler member has assumed said convoluted configuration in said internal cavity of said foldable material bag.

17. The assembly of claim 16 further comprising a handle positioned in said positioning catheter and releasably attached to said filler member.

18. The assembly of claim 17 further comprising an introducer sheath positioned coaxially over said positioning catheter and said pusher catheter.

19. The assembly of claim 15 wherein said filler member has a preformed hook-shaped distal portion.

20. A vascular occlusion assembly comprising:
a foldable material bag of rip stop nylon material having an expanded, diamond shape; an internal cavity; a neck; and an external opening communicating with said internal cavity through said neck;
a wire wrap fixedly positioned around said neck;
a positioning catheter having a flared distal end positioned in said internal cavity of said foldable material bag through said external opening;
a pusher catheter coaxially positioned around said positioning catheter;
a filler member formed from a solid material positioned in said positioning catheter and having a preformed hook-shaped distal portion, said filler member when positioned in said internal cavity of said bag assuming a convoluted configuration expanding said foldable material bag to said expanded, diamond shape without being fixedly secured thereto, said bag with said filler material positioned therein adapted to be placed within the vascular system to occlude the same; and
a handle positioned in said positioning catheter and releasably attached to said filler member.

* * * * *